United States Patent
Sakaguchi et al.

(10) Patent No.: US 10,016,316 B2
(45) Date of Patent: Jul. 10, 2018

(54) DISPOSABLE DIAPER

(71) Applicant: UNICHARM CORPORATION, Shikokuchuo-shi, Ehime (JP)

(72) Inventors: Satoru Sakaguchi, Kanonji (JP); Yasuhiro Yamanaka, Kanonji (JP); Kana Sawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 485 days.

(21) Appl. No.: 14/432,185

(22) PCT Filed: Sep. 27, 2013

(86) PCT No.: PCT/JP2013/076399
§ 371 (c)(1),
(2) Date: Mar. 27, 2015

(87) PCT Pub. No.: WO2014/051105
PCT Pub. Date: Apr. 3, 2014

(65) Prior Publication Data
US 2015/0238367 A1  Aug. 27, 2015

(30) Foreign Application Priority Data

Sep. 28, 2012 (JP) .................................. 2012-218839

(51) Int. Cl.
*A61F 13/15* (2006.01)
*A61F 13/49* (2006.01)
(Continued)

(52) U.S. Cl.
CPC .. *A61F 13/49007* (2013.01); *A61F 13/15585* (2013.01); *A61F 13/49* (2013.01);
(Continued)

(58) Field of Classification Search
CPC .......... A61F 13/49007; A61F 13/15585; A61F 13/49; A61F 13/53; A61F 13/84; A61F 2013/8497; A61F 2013/49053
(Continued)

(56) References Cited

U.S. PATENT DOCUMENTS

| | | | |
|---|---|---|---|
| 4,762,521 A | 8/1988 | Roessler et al. | |
| 2004/0064126 A1* | 4/2004 | Fletcher | A61F 13/496 604/389 |

(Continued)

FOREIGN PATENT DOCUMENTS

| | | |
|---|---|---|
| JP | 63-11151 A | 1/1998 |
| JP | 2003-199791 A | 7/2003 |

(Continued)

OTHER PUBLICATIONS

Office Action in Saudi Arabian Patent Application No. 515360201, dated Jul. 20, 2016, for which abstract in English is attached.
(Continued)

*Primary Examiner* — Jacqueline Stephens
(74) *Attorney, Agent, or Firm* — Hauptman Ham, LLP

(57) ABSTRACT

A disposable diaper (10) in this invention is comprising designs (300a, 300b) that are visually recognizable from a non-skin contact surface side S of the disposable diaper (10) is provided in a region spanning a crotch region (25) and extending to a front waistline region (20) and a rear waistline region (30). A method of arranging the design (300b) provided in a region closer to a side of the front waistline region (20) than the crotch stretching unit (200a) is configured to be different from a method of arranging the design (300a) provided in a region closer to a side of the rear waistline region (30) than the crotch stretching unit (200a).

14 Claims, 7 Drawing Sheets

(51) Int. Cl.
    *A61F 13/514*     (2006.01)
    *A61F 13/53*     (2006.01)
    *A61F 13/84*     (2006.01)

(52) U.S. Cl.
    CPC ........ *A61F 13/51496* (2013.01); *A61F 13/53* (2013.01); *A61F 13/84* (2013.01); *A61F 2013/4905* (2013.01); *A61F 2013/49046* (2013.01); *A61F 2013/49053* (2013.01); *A61F 2013/8497* (2013.01)

(58) Field of Classification Search
    USPC ............ 604/385.24, 385.25, 385.26, 385.27
    See application file for complete search history.

(56) References Cited

U.S. PATENT DOCUMENTS

| | | | | |
|---|---|---|---|---|
| 2005/0065489 | A1* | 3/2005 | Driskell | A61F 13/42 604/361 |
| 2012/0173249 | A1 | 7/2012 | Popp et al. | |
| 2012/0283682 | A1 | 11/2012 | Otsubo et al. | |

FOREIGN PATENT DOCUMENTS

| | | | |
|---|---|---|---|
| JP | 2006-271898 | A | 10/2006 |
| JP | 2007-195738 | A | 8/2007 |
| JP | 2008-136515 | A | 6/2008 |
| JP | 2008-183332 | A | 8/2008 |
| JP | 2008-200410 | A | 9/2008 |
| JP | 2008-253289 | A | 10/2008 |
| JP | 4223405 | B2 | 2/2009 |
| JP | 2010-284430 | A | 12/2010 |
| JP | 2011-147516 | A | 8/2011 |

OTHER PUBLICATIONS

Office Action in EP Patent Application No. 13841222.6, dated Nov. 11, 2016.
Office Action in Chinese Application No. 201380046809.1, dated Apr. 5, 2016.
Office Action in Saudi Arabian Application No. 515360201,dated Apr. 24, 2016, for which an Explanation of Relevancy is attached.
International Search Report dated Dec. 24, 2013, corresponding International Application No. PCT/JP2013/076399.
Written Opinion dated Dec. 24, 2013, corresponding International Application No. PCT/JP2013/076399.
Office Action dated Jan. 22, 2013, corresponding to Japanese patent application No. 2012-218839.
Extended European Search Report in EP Application No. 13841222. 6, dated May 6, 2016.
Office Action in TW Patent Application No. 102135076, dated Feb. 14, 2017.
Office Action in AU Patent Application No. 2013320887, dated Feb. 17, 2017.
Office Action in AU Application No. 2013320887, dated Sep. 26, 2017, 3pp.
Office Action in AU Application No. 2013320887, dated Dec. 21, 2017, 4pp.
Office Action in ID Application No. P-00201501301, dated Apr. 5, 2018, 4pp.

* cited by examiner

DISPOSABLE DIAPER

RELATED APPLICATIONS

The present application is a national phase of International Application Number PCT/JP2013/076399, filed Sep. 27, 2013, which claims priority to Japanese Application Number 2012-218839, filed Sep. 28, 2012.

TECHNICAL FIELD

The present invention relates to a disposable diaper.

BACKGROUND ART

Conventionally, there has been known such a disposable diaper having a front waistline region, a rear waistline region, and a crotch region positioned between the front waistline region and the rear waistline region, the disposable diaper being provided with a pair of leg hole openings while including an absorber spanning the crotch region to extend toward the front waistline region and the rear waistline region.

Herein, Patent Literature 1 describes a technique of providing such a disposable diaper with a design for helping a wearing helper to put the disposable diaper on a wearer.

CITATION LIST

Patent Literature

[Patent Literature 1] Japanese Patent No. 4223405

SUMMARY OF INVENTION

However, a design provided to the disposable diaper described in Patent Literature 1 is provided without consideration of function of this disposable diaper and an appropriate wearing position on the body of a wearer, so that even when a wearing helper tries to put the disposable diaper described in Patent Literature 1 on the wearer with reference to the design, there exists a problem that they cannot put it in an appropriate position on the body of the wearer.

That is, there exists a problem that the design provided to this disposable diaper and the appropriate wearing position on the body of a wearer do not correspond to each other; on the contrary, it gives an impression that the disposable diaper is not worn appropriately.

The present invention has been achieved in consideration of such circumstances, and an object thereof is to provide a disposable diaper that can be worn in an appropriate position on the body of a wearer with reference to a design.

The first character of this invention is summarized as a disposable diaper comprising a front waistline region, a rear waistline region, a crotch region positioned between the front waistline region and the rear waistline region, a pair of leg hole openings, an absorber spanning the crotch region and extending to the front waistline region and the rear waistline region, a product longitudinal direction extending from the front waistline region to the rear waistline region, and a product widthwise direction perpendicular to the product longitudinal direction, wherein:
a stretchable crotch stretching unit that is formed in a region in which the absorber is arranged in the crotch region is provided, a design that is visually recognizable from a non-skin contact surface side of the disposable diaper is provided in a region spanning the crotch region and extending to the front waistline region and the rear waistline region, and a method of arranging the design provided in a region closer to a side of the front waistline region than the crotch stretching unit is configured to be different from a method of arranging the design provided in a region closer to a side of the rear waistline region than the crotch stretching unit.

The second character of this invention is summarized as a disposable diaper comprising a front waistline region, a rear waistline region, a crotch region positioned between the front waistline region and the rear waistline region, a pair of leg hole openings, an absorber spanning the crotch region and extending to the front waistline region and the rear waistline region, a product longitudinal direction extending from the front waistline region to the rear waistline region, and a product widthwise direction perpendicular to the product longitudinal direction, a stretchable crotch stretching unit that is formed in a region in which the absorber is arranged in the crotch region is provided, a design that is visually recognizable from a non-skin contact surface side of the disposable diaper is provided in a region spanning the crotch region and extending to the front waistline region and the rear waistline region;
a length in the product widthwise direction of the absorber arranged in the crotch region is made smaller than a length in the product widthwise direction of the absorber arranged in the front waistline region and the rear waistline region, the design is a pair of lines extending in the product longitudinal direction, and an interval between the pair of lines is configured to be the smallest in the crotch stretching unit.

DESCRIPTION OF EMBODIMENTS

First Embodiment of Present Invention

Figure 1:
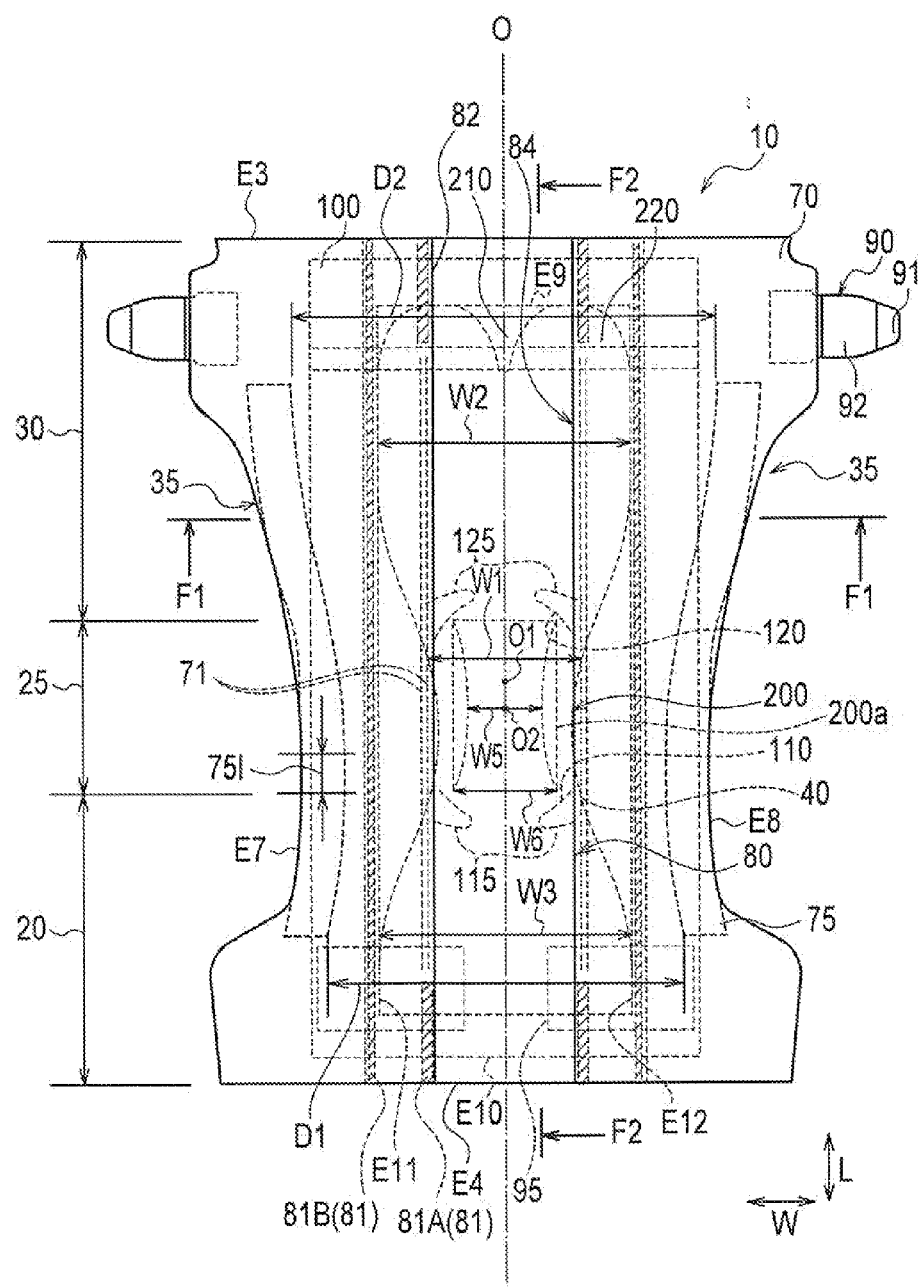
FIG. 1 is an exploded plan view of a disposable diaper according to the present embodiment.

With reference to FIGS. 1 to 5, a disposable diaper 10 according to a first embodiment of the present invention will be explained.

In the following description of the drawings, the same or similar reference numerals are used to designate the same or similar portions. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

It is to be noted that although explanation is made citing a tape-type disposable diaper 10 as an example in the present embodiment, the present invention is also applicable to a pant-type disposable diaper 10.

Figure 2:
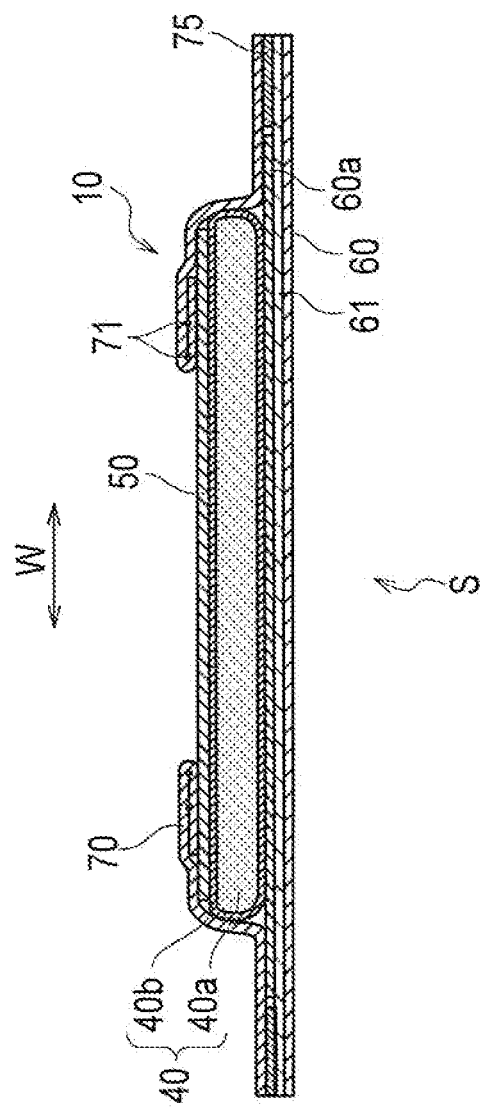
FIG. 2 is a cross-sectional view of the disposable diaper along an F1-F1 line shown in FIG. 1.
Figure 3:
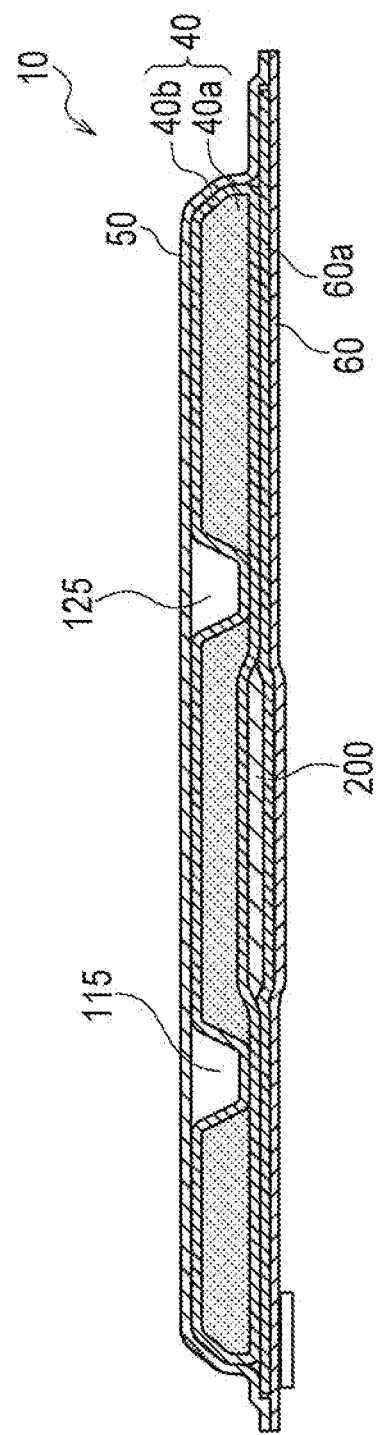
FIG. 3 is a cross-sectional view of the disposable diaper along an F2-F2 line shown in FIG. 1.
Figure 4:
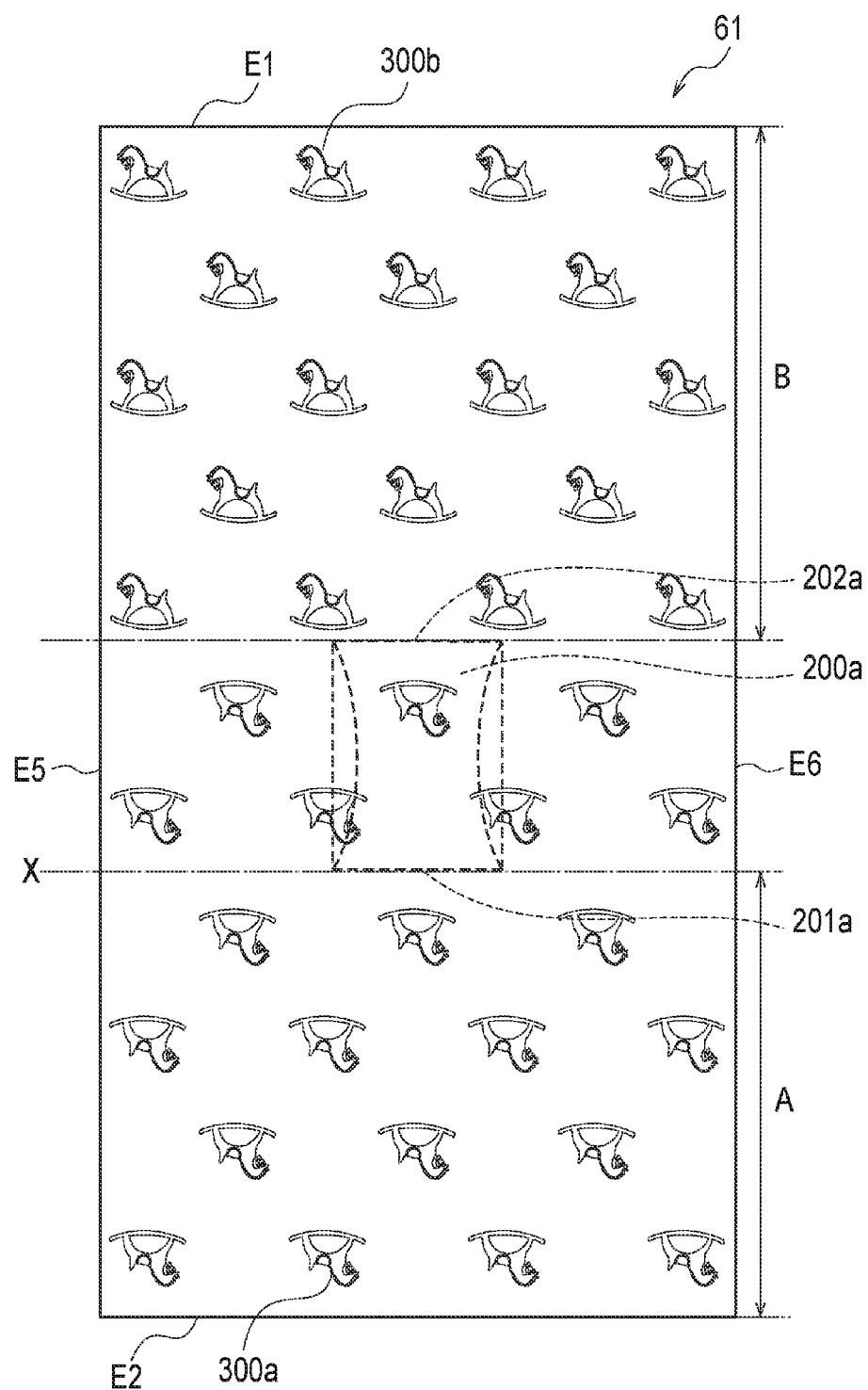
FIG. 4 is a view for illustrating a design provided to the disposable diaper according to the first embodiment of the present invention.
Figure 5:
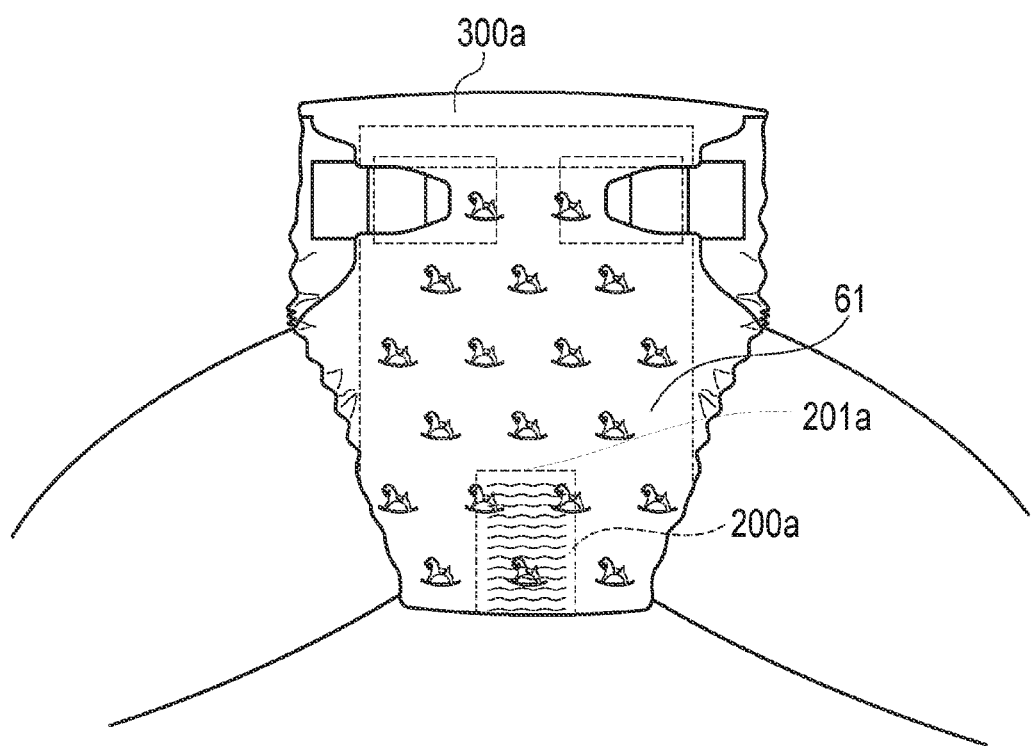
FIG. 5 is a view showing a state in which the disposable diaper according to the first embodiment of the present invention is worn by a wearer.

FIG. 1 is exploded a plan view of a disposable diaper 10 according to the present at least one embodiment. FIG. 2 is a cross-sectional view of the disposable diaper 10 along an F1-F1 line shown in FIG. 1. FIG. 3 is a cross-sectional view of the disposable diaper 10 along an F2-F2 line shown in FIG. 1. FIG. 4 is a view for illustrating a design provided to the disposable diaper according to the first embodiment of the present invention. FIG. 5 is a view showing a state in which the disposable diaper according to the first embodiment of the present invention is worn by a wearer.

It should be noted that the exploded plan view of FIG. 1 is a diagram in which leg stretch unit 75 and elastic member 80 of leg side gathers 80 are in an expanded state such that wrinkles are not formed in a topsheet 50 and side flaps 70, for example, that configure the disposable diaper 10.

As shown in FIG. 1, the disposable diaper 10 includes a front waistline region 20, a crotch region 25, and a rear waistline region 30.

Herein, the front waistline region 20 is a portion that is in contact with the front waistline (ventral portion) of the wearer. Furthermore, the rear waistline region 30 is a portion that is in contact with the rear waistline (dorsal portion) of the wearer. The crotch region 25 is positioned between the front waistline region 20 and the rear waistline region 30.

In the present embodiment, the direction from the front waistline region 20 to the rear waistline region 30 is called a product longitudinal direction L, and the direction perpendicular to the product longitudinal direction L is called a product widthwise direction W.

Herein, a crotch unit 200 is formed within the crotch region 25, and a region closer to a ventral side of a wearer than the crotch unit 200 is defined as a front waistline region 20 while a region closer to a dorsal side of the wearer than the crotch unit 200 is defined as a rear front waistline region 30.

Furthermore, a pair of leg hole openings 35 is formed in the disposable diaper 10. The leg hole openings 35 are provided to side ends in the product widthwise direction W of the disposable diaper, respectively, and are parts that are arranged along the leg holes of a wearer in a state where the disposable diaper 10 is worn by the wearer.

The disposable diaper 10 includes an absorber 40 running across the crotch region 25 and extending from the crotch region towards at least one of the front waistline region 20 and the rear waistline region 30. As shown in FIG. 1, the absorber 40 is configured by an absorbent core 40a and a core wrap 40b.

The absorbent core 40a is the same as that in the conventional disposable diaper, and can be configured appropriately by using well-known components and materials, such as ground pulp and high absorbent polymer. The absorbent core 40a is wrapped by the sheet-like core wrap 40b.

The core wrap 40b is a sheet for covering the absorbent core 40a. A part of at least the skin surface side of the core wrap 40b is configured by various nonwoven fabrics having permeability or a tissue sheet The core wrap 40b is a sheet for covering the absorbent core 40a. A part of at least the skin surface side of the core wrap 40b is configured by various nonwoven fabrics having permeability or a tissue sheet.

As shown in FIGS. 2 and 3, on the top side (skin contact surface side) of the absorber 40 is provided a liquid-permeable topsheet 50. Furthermore, on the back side (non-skin contact surface side) of the absorber 40 is provided a liquid-impermeable backsheet 60a.

A side flap 70 is provided in each side edge in the product widthwise direction W of the absorber 40. The side flaps 70 are made of one or two or more pieces of nonwoven fabrics overlapping one another.

Furthermore, as shown FIG. 1, in a fastening tape 90 is provided in each of the pair of side flaps 70.

The fastening tape 90 extends along the product widthwise direction W in the rear waistline region 30, and holds the disposable diaper 10 onto the body of the wearer by being secured to a target unit 95 of the front waistline region.

The target units 95 are positioned at the non-skin contact surface within the front waistline region 20 and are configured so that the pair of fastening tapes 90 are fixed thereto, respectively.

In the present embodiment, a waistline retaining unit is made up of the front waistline region 20, the rear waistline region 30, and the fastening tapes 90.

Herein, the waistline restraining unit in the rear waistline region 30 corresponds to a range extending in the widthwise direction from a region provided with engaging members of the fastening tapes 90. The waistline retaining unit in the front waistline region 20 corresponds to a range extending in the widthwise direction from a region provided with the target units 95.

Furthermore, as shown in FIG. 1, the disposable diaper 10 according to the present embodiment includes a crotch stretching unit 200a that is formed in the crotch region 25 and is stretchable.

Specifically, the crotch stretching unit 200a is formed within the crotch unit 200, more specifically, within an absorber-arranged region in which the absorber 40 is arranged within the crotch region 25. It is to be noted that a configuration of the crotch stretching unit 200a will be explained later in detail.

Furthermore, as shown in FIG. 1, a surface side of the absorber 40 (a side of the topsheet 50) includes a pair of leg stretching units (leg gathers) 75 that are formed along the leg hole openings 35 and are stretchable at least in the product longitudinal direction L.

The leg stretch units 75 are configured to be longer than the crotch stretch unit 200a in the product longitudinal direction L, and are provided at the outer side from the crotch stretch unit 200a in the product widthwise direction W.

It must be noted that it is sufficient when the leg stretch units 75 are configured such the leg hole openings 35 is stretchable in the product longitudinal direction, and the leg stretch units may be arranged along the leg hole openings 35, or some of the leg stretch units may be arranged in an inclined state with respect to the leg hole openings 35.

Furthermore, the leg stretch units 75 correspond to the portion that is substantially contracted in the product longitudinal direction by a stretchable sheet or the like, and can be conceived as the portion exclusive of the portion in which the stretchable sheet is arranged in a state in which the contractile force is not exhibited.

The configuration of the leg stretch units 75 is described later in detail.

<Leg Side Gather 80>

Additionally, a pair of leg side gathers 80 extending along the product lengthwise direction L may be provided in the inner side of the pair of leg stretch units 75 (closer to the center in the product widthwise direction W).

The leg side gathers 80, which are provided in the inner ends in the product widthwise direction W of the side flaps 70, are upright stretchable gathers arranged on the inner side in the product widthwise direction from the leg stretch unit 75.

The leg side gathers 80 can adopt the conventionally-known structure. Specifically, the leg side gathers 80 it may be made from a sheet member which is different from that of the side flap 70.

The side flaps are folded back to the side of the topsheet in the inner ends in the product widthwise direction and are formed by laminating two layers. As shown in FIG. 2, an elastic member 71 (see, FIG. 2) in a state of being stretched out in the product longitudinal direction L is provided between laminated pieces of the side flap 70 as shown in FIG. 2. The leg side gathers 80 are made up of the side flaps 70 and the elastic members 71.

Each of the leg side gathers 80 has a joining portion 81 to be joined to the topsheet 50 or the backsheet 60a, and a free end portion 82 having an elastic member arranged therein.

A center part of the free end portion 82 in the longitudinal direction is contracted in the product longitudinal direction by means of the elastic member 71 and configures a contracting unit 84.

When the disposable diaper is worn, each of the leg side gathers 80 rises up with the joining portion 81 as the base end, and the contracting unit 84 of the free end portion 82, as the top, comes in contact with the skin of a wearer. That is, the joining portion serves as the base end for a leg side stretch unit to rise up.

It is to be noted that the contracting unit 84 is a part that is practically contracted in the product longitudinal direction by means of the elastic member 71 and is a concept excluding a part in which the elastic member 71 is arranged with no contraction force exerted.

Furthermore, the joining portion 81 in which the side flap 70 and the topsheet 50 (or the backsheet 60a or the like) are bonded together in the leg side gather is marked with diagonal lines and shown in FIG. 2.

The plurality of joining portions 81 are provided, in which a first joining portion 81A is arranged on the outer side in the product longitudinal direction of the contracting unit 84 while a second joining portion 81B is arranged on the outer side in the product widthwise direction of the contracting unit 84.

Therefore, each of the leg side gathers 80 is configured so that the center part including the crotch region 25 in the product longitudinal direction rises up towards a wearer's side.

Of the joining portions 81 of the leg side gathers 80, the first joining portion 81A arranged on the outer side in the product longitudinal direction of the contracting unit 84 is joined to the topsheet 50.

Of the joining portions 81 of the leg side gathers 80, the second joining portion 81B arranged on the outer side in the product widthwise direction of the contracting unit 84 is arranged between the crotch stretch unit 200a and the leg stretch unit 75 in the product widthwise direction W.

The full length in the product longitudinal direction of the second joining portion 81B is joined to the backsheet 60a (and partially to the exterior sheet 60). The backsheet 60a, which is arranged between the absorber 40 and an exterior sheet 60 functions as a leakage-preventing sheet.

Various types of configurations can be adopted for the joining portion 81 of the leg side gathers 80. The joining portion, for example, is configured to be an upright proximal end, and could be a portion extending from the crotch region 25 to the front waistline region and the rear waistline region in the product longitudinal direction and joined with the topsheet, or a portion joined with the liquid-impermeable backsheet and the exterior sheet in the outer side in the widthwise direction from the absorbent core 40a.

Furthermore, the leg side gathers are not limited to the above configuration as long as the leg side gathers are upright gathers arranged on the inner side in the product widthwise direction from the leg stretch unit, and any configuration of the leg side gathers that is well-known in the conventional art can surely be adopted.

<Waist Stretch Unit (Waistline Gather) 100>

The disposable diaper 10 may provide a waist stretch unit 100 that can expand and contract in the product widthwise direction in rear waistline region 30.

Specifically, the waist stretching unit 100 is provided between a pair of fastening tapes 91 in the product widthwise direction W, and is configured so as to contract an interval between the fastening tapes 91 in the product widthwise direction W.

In the present embodiment, the waist stretch unit 100 is made from a stretch sheet. A member configuring the waist stretch unit 100 is not particularly limited but it is preferable to use something as thin as possible, which has the low bending stiffness and the small reduction in width.

By configuring the waist stretch unit 100 from a member having the low bending stiffness, the waist stretch unit 100 can be easily bent along the body, thereby being able to fit along the body without putting the load on the body of a wearer.

Furthermore, by making the waist stretch unit 100 from a member having the small reduction in width, the disposable diaper 10 can be prevented from contracting in the product longitudinal in a case of the disposable diaper 10 being stretched out in the product widthwise direction, so that the disposable diaper can be prevented from hanging down towards the crotch side within the waistline of the wearer.

In the embodiment, as the waist stretch unit 100, an extendable film of 20 to 45 g/m2 in base weight was employed.

After being extended up to 1.25 to 2.5 times the length in the non-expanded state (natural state), the waist stretch unit 100 is adhered onto the waist stretch unit 100 with a hot-melt adhesive or heat processing.

In the present embodiment, the waist stretch unit 100 is arranged between the exterior sheet 60 and the backsheet 60a. However, if the core wrap 40b is configured to extend in the outer side in the product longitudinal direction from the absorbent core 40a, the waist stretch unit 100 may be arranged between the core wrap 40b and the backsheet 60a (or exterior sheet 60).

The position of the waist stretch unit 100 is not particularly restricted. Furthermore, in a region in which the absorber is not arranged, the waist stretch unit 100 may be arranged between the side flaps 70 and the backsheet 60a (or exterior sheet 60).

It is to be noted that, although the waist stretching unit 100 according to the present embodiment is configured to be stretched in the product widthwise direction W, it may be configured so as to be stretched in both of the product widthwise direction W and the product longitudinal direction L.

<Low Rigidity Region 210 in Absorber 40>

Herein, the absorber 40 has a low rigidity region 210 in the rear waistline region 30, the low rigidity region 210 having a smaller total weight than the other area of the absorber 40 or having no existence of the absorbent core 40a.

Furthermore, the low rigidity region 210 is formed so as to extend up to the vicinity of an end E9 at the side of the rear waistline region 30 in the product longitudinal direction L of the absorber 40.

A width of the low rigidity region 210 in the product widthwise direction W becomes larger as approaching the end E9 at the side of the rear waistline region 30 in the product longitudinal direction L of the absorber 40.

More specifically, a shape of the low rigidity region 210 is a wedge shape in the plan view of the disposable diaper.

Furthermore, the absorber 40 has a stretch suppression region 220 as a region in which stretch in the product widthwise direction W is suppressed as compared to the other region.

Herein, the stretch suppression region 220 is formed at each of the outer sides in the product widthwise direction W of the low rigidity region 210, as shown in FIG. 1.

Furthermore, a boundary between the stretch suppression region 220 and the low rigidity region 210 is formed in an arc shape projecting toward the center in the product widthwise direction W. Yet further, the absorber 40 positioned outside the low rigidity region 210 in the product widthwise direction W is formed in a trapezoidal shape projecting toward the end E9 at the side of the rear waistline region 30.

With such a configuration, a wearing helper can be given an image of a shape of the buttocks of a wearer.

Especially in a case of the disposable diaper 10 being the tape-type disposable diaper 10, at the time of spreading the disposable diaper 10 under the body of a wearer, the absorbent core 40a is set in the above-described shape or the waist stretching unit 100 of the rear waistline region 30 is set in the above-described shape, so that a wearing helper can be reminded of a position in which the buttocks of the wearer should be placed, thereby making it possible to put the disposable diaper 10 in a more appropriate position.

It is to be noted that the waist stretching unit 100 and the absorber 40 are configured so as to at least partially overlap with each other in a planar view of the disposable diaper 10.

Specifically, the waist stretching unit 100 is configured so as to overlap with at least a part of the low rigidity region 210 in a planar view of the disposable diaper 10.

It is to be noted that, although the waist stretching unit 100 is arranged so as to overlap with a part of the low rigidity region 210 in the present embodiment, it may be arranged so as to overlap with the whole of low rigidity region 210.

Owing to formation of the low rigidity region 210 described above, stretch of the waist stretching unit 100 is not interrupted, and the low rigidity region 210 is narrowed even when the waist stretching unit 100 is contracted, thereby narrowing an interval between pieces of the absorber 40 outside the low rigidity region 210 in the product widthwise direction W, so that the absorber 40 hardly rises up in an unintended shape.

It is to be noted that, in consideration of preventing the leakage of bodily waste, the low rigid region 210 preferably has a smaller width than that of the waist stretching unit 100.

Furthermore, when the absorber 40 is contracted by the waist stretching unit 100 in the product widthwise direction W to narrow the interval between the pieces of the absorber 40 outside the low rigidity region 210 in the product widthwise direction W, within the low rigidity region 210, the area closer to the end E9 at the side of the rear waistline region 30 is greatly pulled near the center in the product widthwise direction W as compared to the area closer to the crotch region 25, thereby causing a difference in a contraction amount in the product widthwise direction W between the area closer to the end E9 at the side of the rear waistline region 30 and the area closer to the crotch region 25, so that the rear waistline region 30 rises up.

That is, since the disposable diaper 10 is provided with the waist stretching unit 100 that is stretchable in the product widthwise direction W, and the low rigidity region 210 that is formed in a wedge shape, a cup shape in which the disposable diaper 10 expands toward the non-skin contact surface side S is more likely to be formed at the time of wearing the disposable diaper 10.

Furthermore, in the present embodiment, in the low rigidity region 210, the absorbent core 40a does not exist while the waist stretching unit 100 exists so as to overlap with the low rigidity region 210. Therefore, in the low rigidity region 210, the area closer to the end E9 at the side of the rear waistline region 30 is greatly pulled near the center in the product widthwise direction W as compared to the end position of the absorbent core 40a, thereby making rise-up of the rear waistline region 30 more prominent, so that formation of the cup shape can be achieved more stably.

In the present embodiment, the waist stretch unit 100 exists over the side edge in the product widthwise direction W of the absorbent core 40a, so that the disposable diaper 10 can be formed in a cup shape while the absorbent core 40a in a position closer to the end E9 at the side of the rear waistline region 30 in the product longitudinal direction L can be made to actively follow the body of a wearer Furthermore, at least a part of the waist stretching unit 100 and the low rigid region 210 exists in a region extending from the pair of fastening tapes 90 in the product widthwise direction.

Therefore, even at the time when the disposable diaper 10 is put on a wearer in a state where the wearer is laid down on the disposable diaper 10 spread underneath, the waist stretching unit 100 existing over the side edge in the product widthwise direction W of the absorbent core 40a is not spread under the body of the wearer.

Accordingly, the side edge of the waist stretching unit 100 is stretched out by pulling the pair of fastening tapes 90, which makes it easy to make a position closer to the side of the waist within the cup shape be made to follow the body of a wearer more certainly.

In the present embodiment, the absorbent core 40a outside the low rigidity region 210 in the product widthwise direction W is formed in a shape projecting toward the side of the rear waistline region 30. Therefore, as described above, in addition to the fact that the cup shape in which the disposable diaper 10 expands toward the non-skin contact surface side S is easily formed, a surface area of the absorbent core 40a is maintained, so that the leakage of bodily waste from the end of the absorbent core 40a can be prevented.

In the present embodiment, the low rigidity region 210 is formed in a wedge shape in a planar view of the disposable diaper 10, and a boundary between the absorbent core 40a and the low rigidity region 210 is formed in an arc shape so as to project toward the crotch region 25. It is to be noted that a radius of the arc is 50 mm to 200 mm.

Therefore, a length (width) in the product widthwise direction W of the low rigidity region 210 (in a natural state) becomes larger in a non-linear manner as approaching the end E9 at the side of the rear waistline region 30 in the product longitudinal direction L, thereby making rise-up of the rear waistline region 30 more prominent, so that the cup shape can be easily formed more stably.

Furthermore, since the boundary between the absorbent core 40a and the low rigidity region 210 is formed in an arc shape projecting toward the crotch region 25, the rear waistline region 30 is formed in an round cup shape because of contraction of the low rigidity region 210, thereby resulting in a shape which can easily follow the round buttocks of a wearer.

Furthermore, formation of the low rigidity region 210 results in formation of a shape projecting toward the side of the rear waistline region 30 at each of left and right sides, in the end E9 at the side of the rear waistline region 30 of the absorber 40. Such a shape of the absorber 40 reminds of placing the buttocks of a wearer, thereby producing an effect that a wearing helper can easily position the disposable diaper 10 in a more appropriate position for a wearer.

<A Bending Rigidity of the Absorber 40>

The bending rigidity in the present embodiment is based on the rigidity value conforming to the Taber method (JISP8125), and can also be checked by measuring as described below.

First of all, with the disposable diaper 10 in the exploded state, a sample of the portion where the bending rigidity is to be measured (for example, the absorber 40) is extracted.

As regards the sample, the length of the sample in the widthwise direction is 70 mm, the length of the sample in the product longitudinal direction is 38 mm. If a stretchable elastic member is included in the sample, the elastic member is removed. The Taber Stiffness Tester manufactured by Yasuda Seiki Seisakusho Ltd. is used for measuring the rigidity value. 10 samples are taken and measurement is performed for each sample, and the average value is set as the rigidity value.

The measurement procedure is as described in (a) through (e) below.
(a) Measure the thickness (A) of the extracted samples.
(b) Next, insert the sample such that the sample is in contact with the center of the chuck (lower) of the tester.
(c) Adjust the total left-right interval between the support roller and the sample to (A)×0.80 (mm).
(d) Appropriately select an auxiliary weight such that the specified load scale is in the range of 15 to 85% of the maximum scale.
(e) Rotate the samples in both left and right directions, stop at the point where the 15° support marked line and the central marking of the pendulum match, and read the value on the tester. Consider the value on the left side of the scale as (B) and the value on the right side of the scale as (C).

The rigidity value is calculated by the below formula:

Formula: Rigidity value (mN·m)=(((B)+(C))/2)×(Auxiliary weight coefficient)×9.81×10$^{-2}$ If a width of 38 mm cannot be acquired for the specimen, perform conversion to the bending moment of 38-mm width.

The higher the rigidity value thus measured, the higher the bending rigidity, and the lower the rigidity value, the lower the bending rigidity.

<Configuration of Fastening Tape and Target Unit>

The fastening tape 90 is installed in the region of the side flaps 70 corresponding to the rear waistline region 30.

Specifically, as shown in FIG. 1, the fastening tape 90 includes a base sheet 91 connected with the side flaps 70, and a hook sheet 92 provided with a plurality of engagement hooks (not shown in the figure), and fixed onto the base sheet 91.

The hook sheet 92 is a region provided with the engaging member and the aforementioned waistline retaining unit is a region extending in the widthwise direction from the hook sheet 92.

The hook sheet 92 is fixed (specifically, joined) with the base sheet 91.

The hook sheet 92 and the base sheet 91 are preferably joined such that the rigidity of the fastening tape 90 does not become more than necessary. Specifically, the hook sheet 92 and the base sheet 91 are preferably joined by a hot-melt adhesive applied intermittently in dot shape, line shape, or spiral shape. The hook sheet 92 and the base sheet 91 may also be joined with a heat seal, for example.

The base sheet 91 is configured by one layer of nonwoven fabrics or two or more plurality of layers of nonwoven fabrics overlapping one another. A nonwoven fabric manufactured by a manufacturing method such as spun bond (SB) or spun bond-melt blown-spun bond (SMS) can be used as the base sheet 91. The basis weight of the nonwoven fabric (or total basis weight in the case of a plurality of layers) configuring the base sheet 91 is 30 to 120 g/m2, and preferably 40 to 90 g/m2.

The target unit 95 is provided at the non-skin contact surface side of the exterior sheet 60 of the front waistline region. The target unit 95, which is configured such that the engagement hooks of the fastening tape are engaged therein, functions as the loop in a hook-and-loop locking system. An air-through nonwoven fabric, for example, can be used as the target unit.

A fibrous nonwoven fabric prepared from polyolefin-based thermoplastic synthetic resin fibers, or a polyolefin-based thermoplastic synthetic resin film, for example, can be used for the target unit 95. Furthermore, the loop provided in the target unit can be formed by a polyolefin-based thermoplastic synthetic resin.

In addition, a bulky nonwoven fabric, which is embossed partially to prevent fluffing on the surface of the nonwoven fabric may be used as the target unit 95.

Furthermore, the target unit can also be formed by forming the exterior sheet 60 of the disposable diaper with a nonwoven fabric, and then printing a design showing the position of attaching the fastening tape 90 on the non-skin contact surface side of the exterior sheet 60, or by arranging the sheet with a design on the non-skin contact surface side of the exterior sheet 60.

<Leg Stretch Unit 75>

The leg stretch units 75 are arranged along the leg hole openings 35 provided on the outer side in the product widthwise direction of the absorber 40 and are configured so as to be stretchable in the product longitudinal direction L.

Each of the leg stretch units 75 has a widthwise inner end region 751 the position of which in the widthwise direction is placed at the innermost in the crotch region.

The leg hole openings 35 and the leg stretch units 75 extend towards the outer side in the product widthwise direction W especially in the rear waistline region as extending from the crotch region 25 towards the outer side in the product longitudinal direction L It is to be noted that the widthwise inner end region 751 of the leg stretch unit 75 may be arranged in a continuous manner in the product longitudinal direction or may be arranged in non-continuous manner in the product longitudinal direction.

In the present embodiment, the region the position of which in the widthwise direction of the leg hole opening 35 is placed at the innermost in the crotch region corresponds to the widthwise inner end region 751 of the leg stretch unit 75 but may not necessarily correspond.

The leg stretch units 75 of the present embodiment are configured by a stretchable sheet. For example, a stretch film formed by melting a thermoplastic elastomer resin, such as urethane and styrene, and then converting into the shape of a film, a stretchable nonwoven fabric formed from stretchable fibers, or a composite sheet formed by pasting together inextensible sheets that have been partially cut into a stretch film and stretchable nonwoven fabric, or have been made fragile can be used as the stretchable sheet.

Furthermore, instead of the stretchable sheet, a single or a plurality of thread-like or band-like elastic members made of polyurethane elastic fibers and natural rubber may be arranged to configure the leg stretch units 75.

For example, each of the leg stretch units 75 may be made up of a predetermined number of elastic members (for example, three elastic members).

The leg stretch unit 75 is arranged between the side flap 70 and the exterior sheet 60. Alternatively, in a region provided with the backsheet 60a arranged between the absorber 40 and the exterior sheet 60, the leg stretch unit 75 is arranged between the backsheet 60a and the side flap 70.

Specifically, a width of the stretchable sheet member (a width in the product widthwise direction W of the disposable diaper 10 in a natural state) is preferably between 5 mm and 45 mm, more preferably between 12.5 mm and 35 mm at least in the crotch region 25.

It is to be noted that such measurement was performed using a spring tape measure produced by Shinwa Rules Co., Ltd. (a tape unit: glass fiber-contained vinyl chloride coating) in a manner to follow along a measurement object area (10 samples).

When the width of the stretchable sheet member is less than 5 mm, the effect of lowering of the load on the skin by the elastic elements achieved by substantially running, in the form of a surface of the leg stretch units, along the area around the legs of the wearer so as to prevent the partial concentration of the securing force is not exhibited, and when the width of the stretchable sheet member exceeds 45 mm, the region along the area around the legs becomes too wide in comparison to the length in the product widthwise direction of the entire disposable diaper, and as a result, the stretchable sheet member might become entangled at the side of the wearer's body, or may turn over.

The ratio of expansion and contraction of the leg stretch units 75 is preferably 1.5 times to 2.2 times. In the present embodiment, the ratio of expansion and contraction of the leg stretch units 75 is set to 1.8 to 2.0 times.

It is to be noted that a ratio of expansion and contraction means degree of expansion and contraction of the leg stretching unit 75 in an expansion and contraction direction (the product longitudinal direction L in the present embodiment) and is determined as follows.

Ratio of expansion and contraction=(length in the expansion and contraction direction of the leg stretching unit 75 in the maximum stretched state)/(length in the expansion and contraction direction of the leg stretching unit 75 in a natural state)

It should be noted that the ratio of expansion and contraction of the leg stretch units 75, in this specification, is measured as described below.

Firstly, if the disposable diaper 10 is inserted in a package, for example, then the disposable diaper 10 is taken out of the package.

Next, cutting the leg stretch unit 75 arranged region is performed. At this time, cutting is performed by including the exterior sheet 60 joined with the leg stretch unit 75. The ratio of expansion and contraction of the sample including the leg stretch unit after cutting is measured and the ratio of expansion and contraction of the leg stretch unit 75 is calculated.

Each sample is kept for 60 minutes under an atmosphere having a temperature of 20° C.±2° C., and a relative humidity of 60%±5% RH, and the length of the leg stretch unit 75 is measured along the stretching direction. This length is the "Length of the leg stretch unit in the natural state".

Secondly, the length in the stretching direction of the desired region of the disposable diaper in this state (that is, in the natural state), and the length in the stretching direction of the desired region, when the disposable diaper is extended from its natural state until wrinkles caused by the elastic members are not visible on the non-stretchable sheet, are measured. This length is the "Length of the leg stretch unit 75 in the expanded state".

The ratio of expansion and contraction is measured by using these measurement results and calculating according to the formulae described above.

Furthermore, the interval between the inner ends of the pair of the left-right leg stretch units 75 in the product widthwise direction W widens from the crotch region 25 towards the front waistline region 20, and also widens from the crotch region 25 towards the rear waistline region 30.

When the diaper 10 is worn on the body of the wearer, if the leg stretch units 75 are arranged in a shape that is narrower in the crotch unit of wearer and broadens towards the front and rear waistline of wearer, the leg stretch units 75 can be brought closer along the line of the body, and the leg stretch units 75 are elongated and arranged favorably to fit around the legs of the wearer.

Additionally, the interval (D1 in the figure) between the ends of the pair of left-right leg stretch units 75 in the front waistline region 20 is narrower than the interval (D2 in the figure) between the ends of t the pair of left-right leg stretch units 75 in the rear waistline region 30.

It is to be noted that the interval is the distance between the inner ends of the pair of left-right leg stretch units 75 in the product widthwise direction W that is measured after expanding and holding the disposable diaper 10 from the natural state to the state when no wrinkles are formed, in the product longitudinal direction L and the product widthwise direction W.

The extension of the skin surface of the body of the wearer is particularly large in the hip, and is remarkable at a position towards the outer widthwise direction. Furthermore, the leg stretch units 75 are in contact with the body of the wearer. Because D2>D1, even when the movement of the wearer is added to the disposable diaper 10, the leg stretch units 75 in the hip can extend while being in contact with the body, and even when the amount of change in the extension is large, the leg stretch units 75 do not become stiff. Therefore, the shifting of the disposable diaper 10 can be controlled by the leg stretch units 75.

Furthermore, an interval between the both legs of a wearer is shaped so as to become the narrowest in the crotch unit and expand as approaching from the crotch unit to the ventral side and the dorsal side. The leg hole opening unit 35 and the leg stretching unit 75 are shaped so as to extend from the crotch region 25 to the outer side in the product longitudinal direction L and the outer side in the product widthwise direction W, which allows the leg hole opening 35 and the leg stretching unit 75 to be arranged along the leg hole of a wearer, thereby preventing local concentration of stress, achieving close contact with the wearer at a relatively low expansion rate, and making it possible to reduce burden on the skin.

The leg stretch units 75 are configured to contract the disposable diaper 10 by bending it along the leg holes of a wearer. Each of the ends in the product longitudinal direction L of the leg stretch units 75 is arranged so as to expand in the widthwise direction W and arranged in the vicinity of the waistline retaining unit. Therefore, each of the ends in the product longitudinal direction L of the leg stretch units 75 acts so as to contract in the widthwise direction W together with the waistline retaining unit.

<Crotch Stretching Unit 200a>

Next, a shape of the crotch stretching unit 200a will be explained.

The crotch stretching unit 200a is configured to maintain a flat shape in a part of the crotch region 25 at the time of putting the disposable diaper 10 on a wearer, as compared to the other part of the absorber 40.

Herein, the crotch stretching unit 200a may be stretchable in the product longitudinal direction L, may be stretchable in the product widthwise direction W, or may be stretchable in both of the product longitudinal direction L and the product widthwise direction W.

For example, the crotch stretch unit 200a is provided separately and independently of the leg stretch units 75, and is configured to shrink by 60% or more of the length (in natural state) in the widthwise direction of the absorbent core 40a in the position where the crotch stretch unit overlaps the absorbent core 40a (in the present embodiment, it is the position between the core wrap 40b that wraps the absorbent core 40a and the backsheet 60a).

In this way, due to the shrinkage of the portion in which the absorbent core 40a is arranged by the crotch stretch unit 200a, the absorbent core 40a is constricted, and a flat shape is easily maintained as compared to the portion where the absorbent core 40a is not constricted.

On the other hand, the absorbent core 40a positioned in the front waistline region 20 or the rear waistline region 30 that is positioned outside the crotch stretching unit 200a in the product longitudinal direction L is not contracted by the crotch stretching unit 200a.

Therefore, in a state where the disposable diaper 10 is held around the hip or the waist of a wearer by means of the fastening tapes 90, the crotch stretching unit 200a maintained in a flat shape in the crotch region 25 of the disposable diaper 10 does not come in too close contact with the body and as a result, the crotch stretching unit 200a is arranged along the body appropriately.

Furthermore, because the crotch stretch unit 200a is stretchable along the product longitudinal direction L, the front waistline region 20 and the rear waistline region 30 rise up easily due to the shrinkage of the crotch stretch unit 200a. When the disposable diaper is worn, a flat crotch region is formed along the body at the crotch of the wearer.

As a result, the front waistline region 20 and the rear waistline region 30 rise up from the crotch stretching unit 200a, thereby improving the fitting property of the disposable diaper 10 with respect to a wearer.

That is, owing to contraction of the crotch stretching unit 200a, the disposable diaper 10 can be worn stably in a manner that the crotch region 25 of the disposable diaper 10 is arranged in the crotch unit of a wearer.

Furthermore, the crotch stretching unit 200a is configured in a stretchable manner, so that a part of the crotch region 25 of the disposable diaper 10 is contracted to result in formation of uneven wrinkles in the surface of a clothing side (non-skin contact surface side S) of the disposable diaper 10.

As a result, it is possible to remind visually and tactually a wearing helper of the fact that the crotch unit 200 clearly exists in the disposable diaper 10 according to the present embodiment.

It is to be noted that the crotch stretching unit 200a may be made from a stretchable sheet member.

By making the crotch stretching unit 200a from the stretchable sheet member, the absorbent core 40a in the region in which the stretching sheet member is arranged is uniformly contracted, thereby making it easier to maintain a flat shape. It is to be noted that the stretchable sheet member may be made from, for example, a similar stretchable sheet to that of the leg stretching unit 75.

For example, as such a stretchable sheet member, a stretchable film obtained by melting a thermoplastic elastomer resin such as urethane or styrene to form a film shape, a stretchable nonwoven fabric made from stretchy fiber, a composite sheet obtained by pasting an non-stretchable sheet partially cut out or embrittled onto the stretchable film or the stretchable nonwoven fabric, and the like can be used.

Furthermore, rather than the stretchable sheet member, the crotch stretch unit 200a can also be configured by arranging a plurality of thread-like or band-like elastic members made from polyurethane elastic fibers and natural rubber.

In such a case, in consideration of the rigidity of the absorbent core 40a and the rigidity of other components making up the disposable diaper 10, the thickness or arrangement pitch can be arbitrarily selected for an elastic member to be used. However, it is preferable to make the entire region of side edge unit in the product widthwise direction W of the absorbent core 40a be in a contracted state at the time when a main body of the disposable diaper 10 is made in a natural state (non-stretched state).

In addition, in order to uniformly constrict the absorbent core 40a by the crotch stretch unit 200a, the interval between the elastic members is preferably 7 mm or less, and more preferably 5 mm or less. Furthermore, in order to uniformly constrict the absorbent core 40a, the difference in the interval between adjacent elastic members is desired to be 2 mm or less.

The ratio of expansion and contraction of the crotch stretch unit 200a is preferably 1.2 times or more and 1.8 times or less, specifically. In the present embodiment, the ratio of expansion and contraction of the crotch stretch unit 200a is set to 1.4 times.

A ratio of expansion and contraction means degree of expansion and contraction of the crotch stretching unit 200a in the expansion and contraction direction (the product longitudinal direction L in the present embodiment) and is determined as follows.

The ratio of expansion and contraction=(Length of the crotch stretch unit 200a in the maximum stretched state)/(Length of the crotch stretch unit 200a in the natural state)

It should be noted that the ratio of expansion and contraction as used herein is to be measured as described below, for example.

Firstly, if the disposable diaper 10 is inserted in a package, for example, then the disposable diaper 10 is taken out of the package, and the diaper is kept in such a condition for 60 minutes in an atmosphere having a temperature of 20° C.±2° C., and a relative humidity of 60%±5% RH, and the length of the crotch stretch unit is measured along the stretching direction. This length is the "Length of the crotch stretch unit 200a in the stretching direction, in the natural state".

Secondly, the length in the stretching direction of the desired region in this state (that is, in the natural state), and the length in the stretching direction of the desired region, when the open-type disposable diaper is extended from its natural state until wrinkles caused by the elastic members are not visible, are measured. This length is the "Length of the crotch stretch unit 200a in the stretching direction, in the maximum stretched state".

The ratio of expansion and contraction is measured by using these measurement results and calculating according to the formulae described above.

By thus setting the ratio of expansion and contraction of the crotch stretch unit 200a between 1.2 times and 1.8 times, it is possible to favorably follow the stretching of the skin of the wearer.

For example, when the wearer bends forward such that the front side of the body constricts, there exists a part in the skin at the side of the hip portion of the wearer that stretches by approximately 30% as compared to the state when the body has been stretched out.

That is, if the ratio of expansion and contraction of the crotch stretching unit 200a is set 1.2 times or less, contraction of the crotch stretching unit 200a in a natural state is not enough, and in comparison to a case of no crotch stretching unit 200a being provided, contraction of the absorber-arranged region in the crotch region 25 of the disposable diaper 10 is smaller, which makes formation of a flat shape by the crotch region 25 of the disposable diaper 10 become insufficient to follow the body in the crotch unit of a wearer, so that the disposable diaper 10 is more likely to be shifted from the body of the wearer.

On the other hand, when the ratio of expansion and contraction of the crotch stretch unit 200a is more than 1.8 times, the contraction size in the contracting direction of the crotch stretch unit 200a becomes too large, because of which the region where the crotch stretch unit 200a exists easily comes in close contact with the body of the wearer rather than running along it, and the disposable diaper 10 easily shifts to the lower side of the wearer.

Furthermore, the structure may be configured so that the amount of shrinkage in the product longitudinal direction L of the crotch stretch unit 200a is set to 2 to 8% of a length in the product longitudinal direction L of the disposable diaper 10.

It is to be noted that the amount of shrinkage represents a difference between a length "b (mm)" of the sample in the stretched-out state where wrinkles are reduced in number so that the surface of the sample becomes almost smooth and a length "a (mm)" of the sample in the natural state oriented in the direction of expansion and contraction n of the sample, and the amount of shrinkage can be calculated by (b−a). In the present specification, measurement of "length" is performed using a spring measure (a tape measure coated with fiberglass-reinforced vinyl chloride) manufactured by Shinwa Rules Co., Ltd., such that the measure is set along a portion to be measured.

The inventor of the present invention confirmed that the crotch stretch unit 200a is likely to extend suitably along the body of a wearer during a process of putting the disposable diaper 10 on the wearer, in a case where the amount of shrinkage in the product longitudinal direction L of the crotch stretch unit 200a is set to 2 to 8% of a length in the product longitudinal direction L of the disposable diaper 10.

Herein, in a case of the amount of shrinkage in the product longitudinal direction L of the crotch stretch unit 200a being set greater than 8%, the crotch stretch unit 200a shrinks too much to keep sufficient length in the product longitudinal direction L of the disposable diaper 10, thereby making it difficult to put the disposable diaper 10 onto the body of a wearer or making it easy to cause shifting due to too tight contact between the disposable diaper 10 and the body of the wearer in the crotch region 25.

On the other hand, in a case of the amount of shrinkage in the product longitudinal direction L of the crotch stretch unit 200a being smaller than 2%, the crotch stretch unit 200a is less likely to produce the effect to bring the disposable diaper 10 close to the body of a wearer.

Furthermore, a center O2 of the crotch stretching unit 200a in the product longitudinal direction L is arranged closer to the side of the front waistline region 20 as compared to a center O1 of the disposable diaper 10 in the product longitudinal direction L. Furthermore, the crotch stretching unit 200a is arranged so as to span the center O1 of the disposable diaper 10 in the product longitudinal direction L.

Furthermore, the crotch stretch unit 200a is formed in a position including the center O1 of the disposable diaper 10 in the product longitudinal direction L.

Yet further, it is configured that a length (in a natural state) in the product longitudinal direction L of the rear waistline region 30 is longer than a length (in a natural state) in the product longitudinal direction L of the front waistline region 20.

Specifically, a ratio of a length (in a natural state) in the product longitudinal direction L of the rear waistline region 30 to a length (in a natural state) in the product longitudinal direction L of the front waistline region 20 is preferably between 1.1 and 1.6, more preferably between 1.2 and 1.5.

When such a ratio exceeds 1.6, a balance between the ventral side and the dorsal side of the disposable diaper 10 is lost, so that in a case where the crotch stretching unit 200a is positioned along the crotch region 25, the front waistline region 20 comes in too close contact or the rear waistline region 30 is covered more than necessary.

Specifically, the body of a wearer is generally in a state where the buttocks are projecting more than the buttocks, so that the disposable diaper 10 is made in a more suitable shape with respect to a complex shape of the body of the wearer by setting the above-described ratio within the aforementioned range on the condition that the crotch stretching unit 200a and the crotch unit of the wearer are positioned to each other.

That is, it is possible to prevent partial projection of the disposable diaper 10 due to the existence of an undersized part or an unnecessary gap between the disposable diaper 10 and the body due to the existence of an oversized part.

Furthermore, especially in a case of infants and toddlers who use the disposable diaper 10 around the time before or after they start walking, it is considered preferable that they take a posture that the body is shaped into a curl oriented to the ventral side, and in such a posture, the skin at a side of the buttocks is more likely to be stretched, so that the disposable diaper 10 is made in a state suitable for the body of infants and toddlers who tend to take such a posture, by setting the above-described ratio within the aforementioned range.

When one example is cited, with respect to a product length of 400 mm (a length in a natural state in the product longitudinal direction L) of the disposable diaper 10, the front waistline region 20 is set to 130 mm (a length in a natural state in the product longitudinal direction L); the crotch unit 200 is set to 80 mm (a length in a natural state in the product longitudinal direction L); and the rear waistline region 30 is set to 190 mm (a length in a natural state in the product longitudinal direction L).

In such a case, a ratio of a length (in a natural state) between the front waistline region 20 and the rear waistline region 30 is approximately 1.46. By setting such a ratio, not only the crotch stretching unit 200a but also the entire of the disposable diaper 10 in the product longitudinal direction L can be made to further follow along the body of a wearer.

That is, with such a configuration, by determining the position in the front-back direction of the crotch stretching unit 200, the disposable diaper 10 is fit appropriately into the body of a wearer, thereby making it possible to achieve more certainly the object of the present invention, that a design of the disposable diaper 10 is caused to work in conjunction.

Since the state where the crotch stretching unit 200a is contracted, is a different mode from the non-contracted state in the absorber-arranged region that is closer to the side of the front waistline region 20 and the rear waistline region 30 than the crotch stretching unit 200a, in a case of putting the disposable diaper 10 on a wearer, it becomes easy to put it in a manner to position the crotch stretching unit 200a to the crotch unit of the wearer.

Furthermore, with such arrangement, in a state where an area of the absorbent core 40a provided with the crotch stretching unit 200a is contracted, the rigidity or thickness of this area becomes different from the rigidity or thickness of the other area of the absorbent core 40a, thereby making it easy for a wearing helper to recognize an area to be fit to the crotch unit of the wearer in the crotch region 25 of the disposable diaper 10.

Furthermore, after the disposable diaper 10 has been worn, the crotch stretching unit 200a maintains its flat shape in the crotch unit of a wearer so the disposable diaper 10 itself as to be in a three-dimensional shape, thereby making it possible to make the crotch region 25 of the disposable diaper 10 follow the crotch unit of the wearer, which makes it more certain that the disposable diaper 10 is wore while the crotch region 25 and the crotch unit of the wearer fit to each other.

Yet further, as shown in FIG. 1, it may be configured that a length W5 (in a natural state) in the product widthwise direction W in the center position O2 of the crotch stretching unit 200a in the product longitudinal direction L is shorter than a length W6 (in a natural state) in the product widthwise direction W at the end of the crotch stretching unit 200a in the product longitudinal direction L.

With such a configuration, since the shape as seen from the exterior of the crotch stretching unit 200a is an hourglass shape like a crotch unit of women's underwear, for example, at the time of putting the disposable diaper 10 on a wearer, it is possible for a wearing helper to put it in a manner that the crotch stretching unit 200a is arranged at the crotch unit of the wearer and to visually confirm that a wearing position is appropriate.

Furthermore, also in while the disposable diaper 10 is worn, it is possible to remind a wearing helper of the fact that the disposable diaper 10 has the crotch unit 200 and to give an image even more like underwear.

As shown FIG. 1, a notch 110 (notch 120) is formed in the crotch region 25 of the absorber 40. The notch 110 and the notch 120 correspond to a region in which the absorbent core 40a configuring the absorber 40 does not exist.

In the present embodiment, the notch 110 and the notch 120 correspond to a low rigidity unit in which the basis weight of the absorbent core 40a is lower than that of the other portion of the absorbent core 40a.

It is to be noted that in place of forming the notch 100 and the notch 120, it may be configured to set a total weight of the absorbent core 40a smaller than the other area of the absorbent core 40a.

As shown in FIG. 1, the notch 110 and the notch 120 are formed along the edge in the product longitudinal direction L of the crotch stretching unit 200a.

It should be noted that even though the notch 110 and the notch 120 are formed, the absorbent core 40a positioned in the front waistline region 20 and the rear waistline region 30, and the absorbent core 40a positioned in the crotch region 25 are preferred to be in continuation, particularly in the widthwise direction, rather than being completely separate.

As the notch 110 and the notch 120 run towards the outer side in the product widthwise direction W, the length in the product longitudinal direction L keeps on widening.

As a result of such a shape, the outer side in the product widthwise direction W of the absorbent core 40a is constricted more easily, and a flat "bottom unit" is formed more easily.

Furthermore, the absorbent core 40a positioned towards the front waistline region 20 from the notch 110, and the absorbent core 40a positioned towards the rear waistline region 30 from the notch 120 rise up from the "bottom unit", and can easily curve along the roundness of the body of the wearer (the abdominal portion and the hip), because of which the shape of the disposable diaper can be brought closer to the body of the wearer.

As shown FIG. 1, the edge towards the front waistline region 20 of the notch 110 and the edge towards the rear waistline region 30 of the notch 120 is arc shaped.

Specifically, the edge at the side of the front waistline region 20 of the notch 110 is shaped so that the center of arc is positioned closer to the side of the rear waistline region 30 as compared to the aforementioned edge, while the edge at the side of the rear waistline region 30 of the notch 120 is shaped so that the center of arc is positioned closer to the side of the front waistline region 20 as compared to the aforementioned edge.

As a result of such a shape, the deformation along the roundness of the body of the wearer occurs more easily and remarkably.

The edge at the side of the front waistline region 20 in the product longitudinal direction L of the notch 110 makes up a first inflection unit 115 while the edge at the side of the front waistline region 30 in the product longitudinal direction L of the notch 120 makes up a second inflection unit 125.

It is to be noted that the first inflection unit 115 and the second inflection unit 125 are configured to extend in the product widthwise direction W to function as a bending base point of the disposable diaper 10.

<Method of Arranging Design>

As shown in FIG. 2, the back surface side (the non-skin contact surface side 5) of the backsheet 60a is provided with one shingle sheet 61 (for example, a film) spanning the crotch region 25 to extend to the front waistline region 20 and the rear waistline region 30, and the back surface side (the non-skin contact surface side 5) of the sheet 61 is provided with an exterior sheet 60.

Herein, in a region which spans the crotch region 25 and extends to the front waistline region 20 and the rear waistline region 30, designs 300a, 300b, which are visually recognizable from the non-skin contact surface side S of the disposable diaper 10, are provided. These designs 300a, 300b are provided on the sheet 61.

Herein, as shown in FIG. 4, a method of arranging the design 300a provided in a region A closer to the side of the front waistline region 20 than the crotch stretching unit 200a and a method of arranging the design 300b provided in a region closer to the side of the rear waistline region 30 than the crotch stretching unit 200a are configured differently from each other.

That is, depending on the designs 300a, 300b, that is, depending on arrangement orientation, size, color, etc., of a pattern, character design, figure, letter, or the like, it is possible to remind a wearing helper of the fact that the region A described above is closer to the side of the front waistline region 20 (the ventral side) of the disposable diaper 10 while reminding of the fact that the region B described above is the side of the rear waistline region 30 (the dorsal side) of the disposable diaper 10.

For example, as shown in FIG. 4, the identical designs 300a, 300b are used between the region A and the region B, and the design 300a provided in the region A and the design 300b provided in the region B may be ones which are rotated 180 degrees with respect to each other. It is to be noted that such a rotation angle may be degrees other than 180 degrees.

For example, in the above manner, by changing a direction of arranging the designs (character designs) 300a, 300b, the designs (character designs) 300a, 300b can be shown in an appropriate direction when a wearer is viewed from the ventral side and the dorsal side after disposable diaper 10 has been worn.

The crotch stretching unit 200a has a front end 201a closer to the front waistline region 20, and a rear end 202a closer to the rear waistline region 30. Herein, as shown in FIG. 4, a method of arranging the designs 300a, 300b may be configured so as to be made different across the border set to the end X (i.e., the front end 201a) at the side of the front waistline region 20 of the crotch stretching unit 200a.

As described above, owing to the function of the crotch stretching unit 200a of the disposable diaper 10, the disposable diaper 10 can be worn while more reliably fitting the ventral unit, the crotch unit, and the dorsal unit of a wearer to the front waistline region 20, the crotch region 25, and the rear waistline region 30 of the disposable diaper 10, thereby being able to realize the disposable diaper 10 in which a design made to match an orientation of the body of a wearer can be arranged.

Therefore, by a wearing helper putting the disposable diaper 10 on a wearer with reference to the designs 300a, 300b described above, the disposable diaper 10 can be put in an appropriate position of the body of a wearer, thereby making it possible to improve leakage from the crotch unit of the wearer or feeling of discomfort at the time of putting the disposable diaper 10 in the crotch unit of the wearer.

Furthermore, owing to the fact that the crotch unit 200 clearly exists and the design is applied to this crotch unit 200, that is, by switching the design applied to the crotch unit 200 between the side of the front waistline region 20 and the side of the rear waistline region 30, its appearance image can be changed from an image of the disposable diaper 10 to an image more like underwear or lingerie, thereby making it possible to give a wearing helper an impression of better feeling of comfort at the time of wearing.

Furthermore, in the vicinities of ends E1, E2 in the product longitudinal direction L of the sheet 61, the above-described designs 300a, 300b are not provided. Yet further, in ends E3, E4 in the product longitudinal direction L of the disposable diaper 10, the sheet 61 is not arranged.

Similarly, in the vicinities of ends E5, E6 in the product widthwise direction W of the sheet 61, the above-described designs 300a, 300b are not provided. Yet further, in ends E7, E8 in the product widthwise direction W of the disposable diaper 10, the sheet 61 is not arranged.

That is, the sheet 61 is arranged so as to cross the ends E9, E10 in the product longitudinal direction L of the absorber 40 and ends E11, E12 in the product widthwise direction W of the absorber 40 while not reaching the ends E3, E4 in the product longitudinal direction L of the disposable diaper 10 and the ends E7, E8 in the product widthwise direction W of the disposable diaper 10.

As described above, by not providing the designs 300a, 300b in the vicinity of the sheet 61 while not arranging the sheet 61 in a position overlapping with the ends of the disposable diaper 10, it is possible to prevent the designs 300a, 300b provided in the sheet 61 from being broken in the outer peripheral end of the disposable diaper 10 and also the designs 300a, 300b from being broken in the boundary between the sheet 61 provided with the designs 300a, 300b and another sheet (nonwoven fabric) making up the disposable diaper 10.

As a result, the designs 300a, 300b broken in boundary to the sheet 61 or the ends of the disposable diaper 10 degrades esthetics of the designs 300a, 300b, while giving a wearing helper an impression of the disposable diaper 10 being made by cutting and pasting together pieces at the time when the wearing helper views the designs 300a, 200b. That is, by arranging the designs 300a, 300b without a break, it is possible to remind the wearing helper of an impression even more like underwear.

Furthermore, since the sheet 61 having the designs 300a, 300b is arranged so as to cover the entire region of the absorber 40, change in color of the absorber 40 due to bodily waste can be made less noticeable, thereby being able to maintain an impression like underwear during use as well.

Furthermore, it is configured that, in comparison to a ratio of the designs 300a, 300b in a region corresponding to the front waistline region 20 and the rear waistline region 30, a ratio of the designs 300a, 300b in a region corresponding to the crotch region 25 having the existence of the crotch stretching unit 200a is set smaller.

With such a configuration, by increasing an ratio of design (a design ratio) in the front waistline region 20 and the rear waistline region 30 which are more likely to stand out at the time of wearing, the front waistline region 20 and the rear waistline region 30 can be emphasized while making the crotch region 25 less noticeable by decreasing a ratio of design (a design ratio) in the crotch region 25.

As a result, in a case where the crotch region 25 is caused to follow along the body of a wearer by means of the crotch stretching unit 200a, it is possible to give an impression that the crotch region 25 is housed with better fit in the crotch unit of a wearer without giving any feeling of discomfort.

As shown in FIG. 5, the disposable diaper 10 according to the present embodiment is configured so as to form a flat "bottom" by means of the crotch stretching unit 200a arranged in the crotch region 25, thereby giving a wearing helper an impression that the front waistline region 20, the crotch region 25, and the rear waistline region 30 are individually independent from each other.

Therefore, by making a method of arranging the designs 300a, 300b be different between regions in front and behind the crotch stretching unit 200a, as shown in FIG. 5, a wearing helper can put the disposable diaper 10 in an appropriate position of the body of a wearer based on the design 300a, 300b.

Furthermore, with the disposable diaper 10 according to the present embodiment, at the time of putting the disposable diaper 10 in an appropriate position of a wearer, designs in the front waistline region 20, the crotch region 25, the rear waistline region 30, and the like of the disposable diaper 10 are arranged without giving any feeling of discomfort, thereby being able to give an impression even more like underwear.

<Method of Manufacturing the Disposable Diaper 10>

Next, an example of the method of manufacturing the disposable diaper 10 according to the present embodiment will be described. As far as the method that is not described in the present embodiment is concerned, the existing method can be used. Furthermore, the manufacturing method explained below is only an example, and the disposable diaper 10 can also be manufactured by other manufacturing methods. The method of manufacturing the disposable diaper 10 includes at least a component forming step, a component loading step, a leg hole forming step, and a cutting step.

In the component forming step, the components configuring the disposable diaper are formed. Specifically, for example, an absorbent material is laminated and the absorber 40 is molded.

In the component loading step, components the configuring the disposable diaper 10, such as the stretch sheet configuring the leg stretch unit 75, other web such as a web configuring the topsheet, a leakage-preventing sheet, an absorber, and the like, are loaded on a web configuring the backsheet.

Specifically, the stretch sheet configuring the leg stretch unit 75 is stretched out and further transferred onto an intermittent drum while being displaced in the widthwise direction, and thereafter the stretch sheet is cut into an individual product length on the intermittent drum.

The stretch sheets are interspaced at intervals in association with rotation of the intermittent drum and transferred onto the continuous web. In this manner, the leg stretch unit can be arranged in a curved line.

In the leg hole opening forming step, the topsheet 50, the exterior sheet 60, and the backsheet 60a are cut along the widthwise outer end of the leg stretch unit 75. In this manner, the leg hole openings 35 arranged at the leg holes of a wearer are formed.

In the cutting step, the continuous body on which the topsheet 50, the backsheet 60a, and the absorber 40 are arranged is cut in the size of one product along the product widthwise direction W. The disposable diaper 10 is thus manufactured.

Second Embodiment of Present Invention

Figure 6:
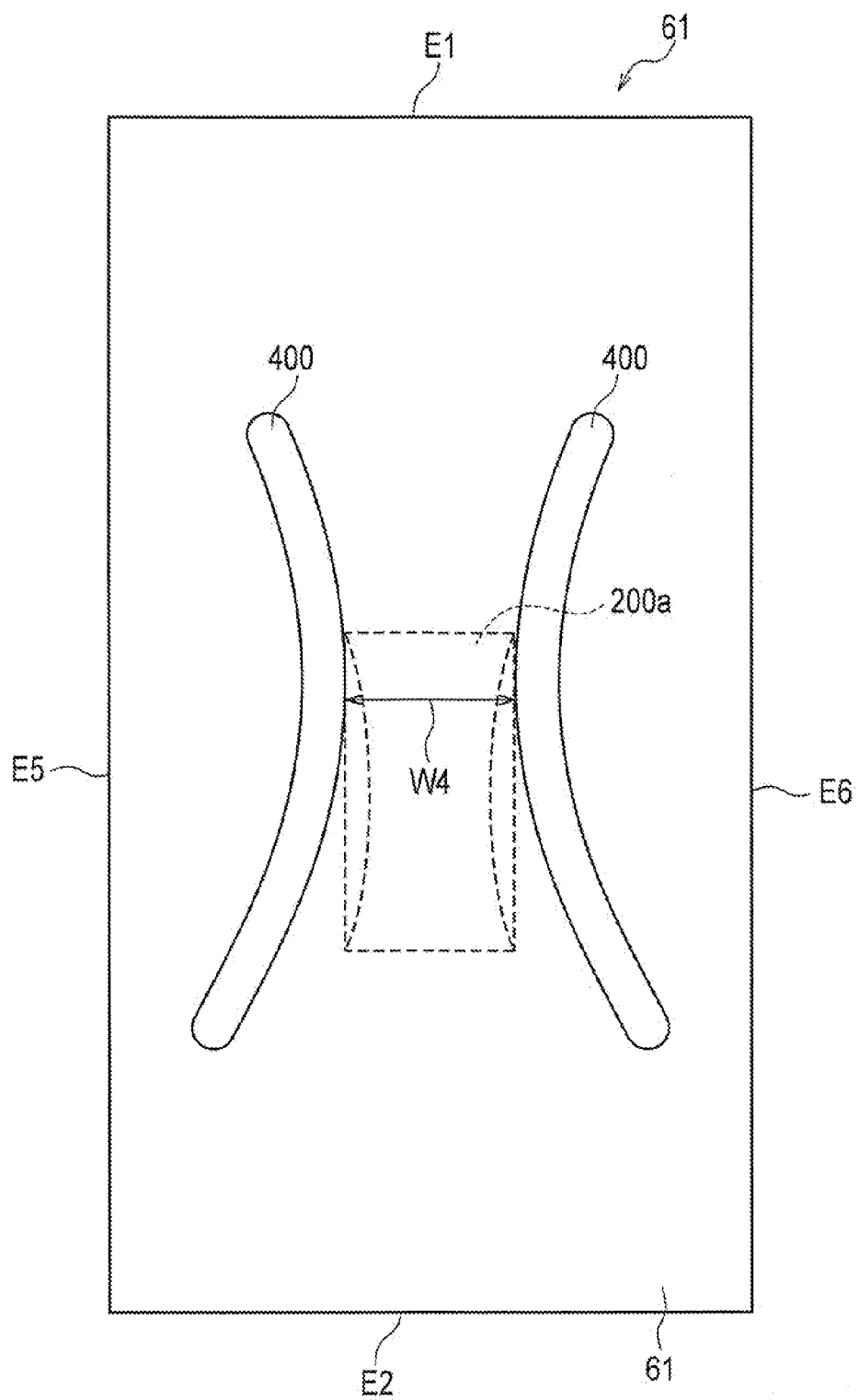
FIG. 6 is a view for illustrating a design provided to a disposable diaper according to a second embodiment of the present invention.

With reference to FIG. 6, a disposable diaper 10 according to the second embodiment of the present invention will be explained. Hereinafter, the disposable diaper 10 according to the second embodiment will be explained with a focus on differences from the disposable diaper 10 according to the second embodiment described above.

The disposable diaper according to the present embodiment is configured that, as shown in FIG. 1, a length W1 (in a natural state) in the product widthwise direction W of the absorber 40 arranged in the crotch region 25 is smaller than lengths W2, W3 (in a natural state) in the product widthwise direction W of the absorber 40 arranged in the front waistline region 20 and the rear waistline region 30.

Specifically, it is preferable that the crotch stretching unit 200a be overlapped with a part having the smallest width (a length in the product widthwise direction W) of the absorbent core 40a.

With such a configuration, the part with the smallest width of the absorbent core 40a and the crotch stretching unit 200a are housed in the crotch unit of a wearer, and a wearing position of the disposable diaper 10 is determined in the crotch unit of the wearer, which makes it more certain that the disposable diaper 10 is put in an appropriate position of the body of the wearer.

Furthermore, as shown in FIG. 6, a design 400 provided in the disposable diaper 10 according to the present embodiment is a pair of curved lines 400 extending in the product longitudinal direction L.

Herein, it is configured that an interval W4 between the pair of lines 400 becomes the smallest in the crotch stretching unit 200a.

Specifically, it may be configured that the interval W4 between the pair of lines 400 becomes the smallest in the end (the first inflection nit 115) at the side of the front waistline region 20 in the product longitudinal direction L of the crotch stretching unit 200a.

With the disposable diaper 10 according to the present embodiment, the interval W4 between the pair of lines 400 in the product widthwise direction W is made to become the smallest in the crotch stretching unit 200a and to expand as approaching the side of the front waistline region 20 and the side of the rear waistline region 30 across the crotch stretching unit 200a as a boundary, so that it is possible to remind a user of the fact that the crotch stretching unit 200a is an element to be arranged in the crotch unit of a wearer and to put the disposable diaper 10 on in a manner to position the crotch stretching unit 200a to the crotch unit of the wearer, and at the same time, it is also possible to remind a wearing helper of the fact that the crotch unit 200 clearly exists at the time of wearing.

Third Embodiment of Present Invention

Figure 7:
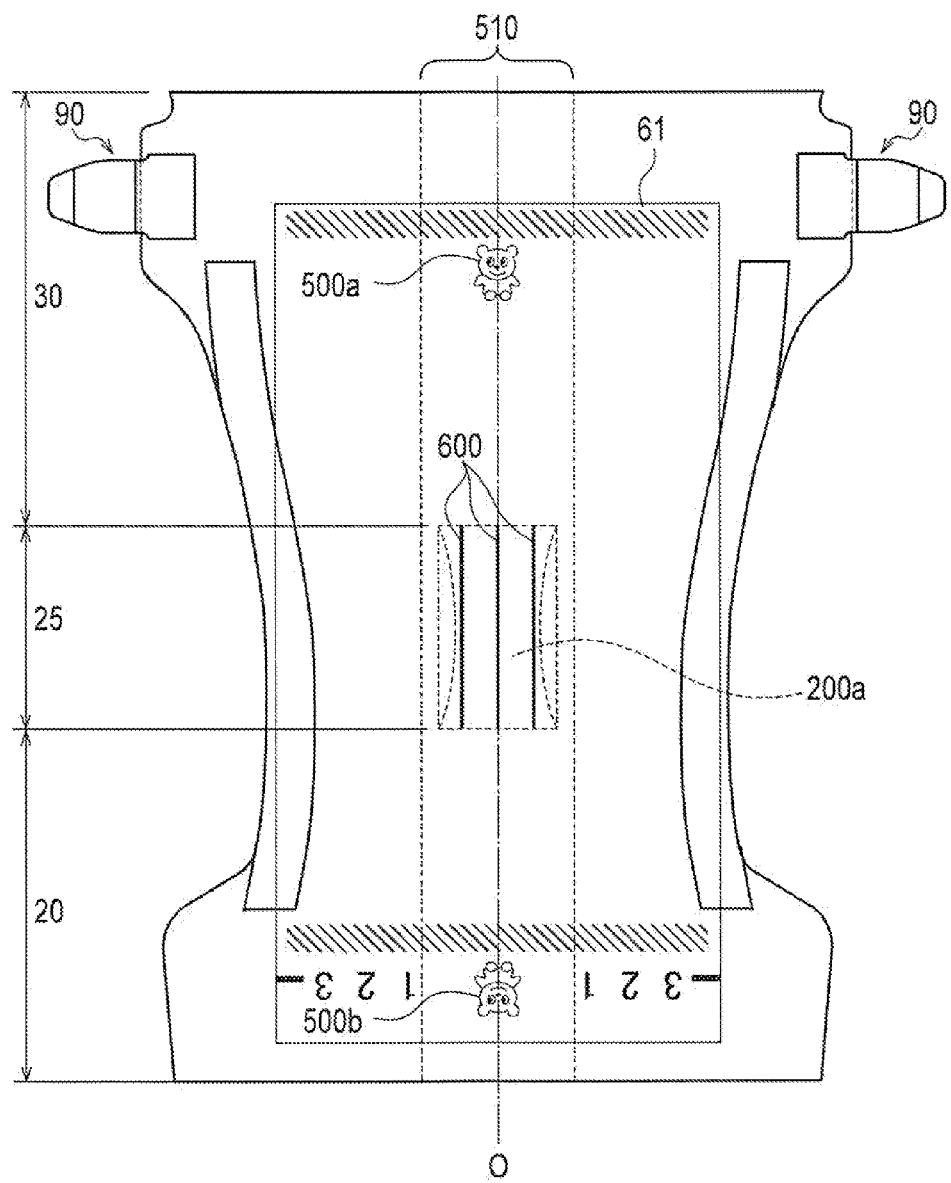
FIG. 7 is a view for illustrating a design provided to a disposable diaper according to a third embodiment of the present invention.

With reference to FIG. 7, a disposable diaper 10 according to the third embodiment of the present invention will be explained. Hereinafter, the disposable diaper 10 according to the third embodiment will be explained with a focus on differences from the disposable diapers 10 according to the first and second embodiments described above.

As shown in FIG. 7, the disposable diaper 10 according to the third embodiment of the present invention is configured so that main patterns 500a, 500b are arranged in the front waistline region 20 and the rear waistline region 30 within a virtual region 510 spanning the crotch stretching unit 200a and extending in the product longitudinal direction.

Herein, in a product natural state, the crotch stretching unit 200 may be symmetrical across the center line O in the product widthwise direction W, or may have a difference of 10% or less between a left width and a right width of the crotch stretching unit 200a while the center line O in the product widthwise direction W is set as a boundary.

With the disposable diaper 10 according to the present embodiment, it is possible to make a state in which the crotch stretching unit 200a is put on the crotch unit of a wearer while spanning the center of the body of the wearer.

Moreover, the main patterns (for example, a larger size of pattern, character design, letter, or the like, or a pattern, character design, letter, figure, or the like which has a different color from other area) 500*a*, 500*b* that draw more attention than other designs are arranged within the virtual region extending from the crotch stretching unit 200*a*, so that it is possible to remind of the fact that the main patterns 500*a*, 500*b* are to be positioned to the center of the side of the front waistline region 20 and the side of the rear waistline region 30 of the disposable diaper 10 as well as the center of the body of a wearer (the front waistline region 20 corresponds to a vicinity of the navel while the rear waistline region 30 side corresponds to a vicinity of the spine).

Furthermore, a wearing helper is reminded of the fact that each of the crotch unit 200, the front waistline region 20, and the rear waistline region 30 of the disposable diaper 10 clearly exists, thereby making it possible to give an impression even more like underwear.

Yet further, as shown in FIG. 7, the disposable diaper 10 according to the third embodiment of the present invention may be configured so that a line pattern 600 which spans the crotch stretching unit 200*a* and extends to the front waistline region 20 and the rear waistline region 30 of the disposable diaper 10 is arranged.

This line pattern 600 may be configured so that, as shown in FIG. 7, a plurality of lines extend substantially in parallel to the center line O in the product widthwise direction W.

With such a configuration, in addition to the fact that positions of the crotch unit, the ventral unit, and the dorsal unit of the body of a wearer can be fit to the position in the product longitudinal direction L of the disposable diaper 10 by means of the crotch stretching unit 200*a*, the horizontal center position in the crotch unit of the wearer can be fit to the position in the product widthwise direction W of the disposable diaper 10.

As described above, it is of course the case that the present invention includes various embodiments and the like not described here. Therefore, the technical range of the present invention is to be defined only by the inventive specific matter according to the adequate claims from the above description.

The present invention can be implemented as corrected and modified modes without departing from the gist and the scope of the present invention defined by the claims. Therefore, the description of the specification is intended for explaining the example only and does not impose any limited meaning to the present invention.

The entire contents of Japanese Patent Application No. 2012-218839 (filed on Sep. 28, 2012) are incorporated in the present specification by reference.

INDUSTRIAL APPLICABILITY

It is possible to provide as a disposable diaper that can be worn in an appropriate position on the body of a wearer with reference to a design.

REFERENCE SIGNS LIST

10: disposable diaper
20: front waistline region
25: crotch region
30: rear front waistline region
35: leg hole opening
40: absorber
40*a*: absorbent core
40*b*: core wrap
50: topsheet
60*a*: backsheet
60: exterior sheet
61: sheet
70: side flap
75: leg stretch unit
80: leg side gathers
81: joining portion
82: free end portion
90: fastening tape
95: target unit
100: waist stretch unit
110,120: notch
115: first inflection unit
125: second inflection unit
200: crotch unit
200*a*: crotch stretch unit
300*a*,300*b*.400: design
500*a*,500*b*: main patterns
600: line pattern

The invention claimed is:

1. A disposable diaper, comprising:
   a front waistline region;
   a rear waistline region;
   a crotch region positioned between the front waistline region and the rear waistline region;
   a pair of leg hole openings;
   an absorber spanning the crotch region and extending to the front waistline region and the rear waistline region;
   a product longitudinal direction extending from the front waistline region to the rear waistline region;
   a product widthwise direction perpendicular to the product longitudinal direction; and
   a stretchable crotch stretching unit disposed in a region in which the absorber is arranged in the crotch region, wherein
   the crotch stretching unit has a front end closer to the front waistline region, and a rear end closer to the rear waistline region,
   designs that are visually recognizable from a non-skin contact surface side of the disposable diaper span the crotch region and extend to the front waistline region and the rear waistline region,
   the design provided closer to the front waistline region is arranged differently from the design provided closer to the rear waistline region to visually indicate the front end of the crotch stretching unit or the rear end of the crotch stretching unit,
   the crotch stretching unit overlaps an area of the absorber in a product thickness direction crossing the product longitudinal direction and the product width direction, and
   the crotch stretching unit is configured to contract in the product widthwise direction to cause the area of the absorber to be constricted.

2. The disposable diaper according to claim 1, further comprising:
   an exterior sheet on a non-skin contact surface side of the absorber; and
   a sheet spanning the crotch region and extending to the front waistline region and the rear waistline region, the sheet being located between the exterior sheet and the absorber,
   wherein
   the absorber has opposite longitudinal ends in the product longitudinal direction, and opposite side ends in the product widthwise direction, the disposable diaper has opposite longitudinal ends in the product longitudinal direction, and opposite side ends in the product widthwise direction, the sheet has opposite longitudinal ends in the product longitudinal direction, and opposite side ends in the product widthwise direction, the sheet extends to cross the longitudinal ends of the absorber and the side ends of the absorber while not reaching the longitudinal ends of the disposable diaper and the side ends of the disposable diaper, and the designs are arranged between the longitudinal ends of the sheet and between the side ends of the sheet while being not arranged in a vicinity of the longitudinal ends of the sheet and a vicinity of the side ends of the sheet.

3. The disposable diaper according to claim 1, wherein the designs have main patterns arranged in the front waistline region and the rear waistline region, and the main patterns are also located in a predetermined region spanning the crotch stretching unit and extending in the product longitudinal direction.

4. The disposable diaper according to claim 1, wherein the crotch stretching unit is stretchable in the product longitudinal direction.

5. The disposable diaper according to claim 1, further comprising a waist stretching unit in the rear waistline region and stretchable in the product widthwise direction, wherein the absorber has a low rigidity region in the rear waistline region, the low rigidity region having a smaller total weight than a remaining area of the absorber or having no existence of an absorbent core;

the waist stretching unit overlaps with at least a part of the low rigidity region in a planar view of the disposable diaper, and a width of the low rigidity region in the product widthwise direction gradually increases as the low rigidity region expands toward a longitudinal end of the absorber at the rear waistline region.

6. The disposable diaper according to claim 1, wherein a contraction amount of the crotch stretching unit in the product longitudinal direction is 2 to 8% of a length of the disposable diaper in the product longitudinal direction.

7. The disposable diaper according to claim 1, wherein a ratio of a length of the rear waistline region in the product longitudinal direction to a length of the front waistline region in the product longitudinal direction is between 1.1 and 1.6.

8. The disposable diaper according to claim 1, wherein the crotch stretching unit has a center position in the product longitudinal direction, and a dimension of the crotch stretching unit in the product widthwise direction in the center position is less than (i) a dimension of the front end of the crotch stretching unit in the product widthwise direction and (ii) a dimension of the rear end of the crotch stretching unit in the product widthwise direction.

9. The disposable diaper according to claim 1, wherein the crotch stretching unit is positioned at a non-skin contact surface side of the absorber.

10. The disposable diaper according to claim 1, further comprising a pair of leg stretch units opposing each other in the product widthwise direction and extending in the product longitudinal direction, wherein the crotch stretching unit is positioned between the leg stretch units and independent from the leg stretch units.

11. The disposable diaper according to claim 1, wherein the designs include a front design provided closer to the front waistline region, and a rea design provided closer to the rear waistline region, the front design includes a pattern, and the rear design includes the same pattern but orientated differently from the pattern of the front design.

12. The disposable diaper according to claim 11, wherein the front end of the crotch stretching unit or the rear end of the crotch stretching unit is located, in the product longitudinal direction, between the differently oriented patterns of the front and rear designs.

13. A disposable diaper, comprising:
a front waistline region;
a rear waistline region;
a crotch region positioned between the front waistline region and the rear waistline region;
a pair of leg hole openings;
an absorber spanning the crotch region and extending to the front waistline region and the rear waistline region;
a product longitudinal direction extending from the front waistline region to the rear waistline region;
a product widthwise direction perpendicular to the product longitudinal direction; and
a stretchable crotch stretching unit disposed in a region in which the absorber is arranged in the crotch region, wherein the crotch stretching unit has a front end closer to the front waistline region, and a rear end closer to the rear waistline region, designs that are visually recognizable from a non-skin contact surface side of the disposable diaper span the crotch region and extend to the front waistline region and the rear waistline region, the design provided closer to the front waistline region is arranged differently from the design provided closer to the rear waistline region to visually indicate the front end of the crotch stretching unit or the rear end of the crotch stretching unit, the crotch stretching unit has a center position in the product longitudinal direction, and a dimension of the crotch stretching unit in the product widthwise direction in the center position is less than (i) a dimension of the front end of the crotch stretching unit in the product widthwise direction and (ii) a dimension of the rear end of the crotch stretching unit in the product widthwise direction.

14. A disposable diaper, comprising:
a front waistline region;
a rear waistline region;
a crotch region positioned between the front waistline region and the rear waistline region;
a pair of leg hole openings;
an absorber spanning the crotch region and extending to the front waistline region and the rear waistline region;
a product longitudinal direction extending from the front waistline region to the rear waistline region;
a product widthwise direction perpendicular to the product longitudinal direction;
a stretchable crotch stretching unit disposed in a region in which the absorber is arranged in the crotch region; and
a pair of leg stretch units opposing each other in the product widthwise direction and extending in the product longitudinal direction, wherein the crotch stretching unit has a front end closer to the front waistline region, and a rear end closer to the rear waistline region, designs that are visually recognizable from a non-skin contact surface side of the disposable diaper span the crotch region and extend to the front waistline region and the rear waistline region, the design provided closer to the front waistline region is arranged differently from the design provided closer to the rear waistline region to visually indicate the front end of the crotch stretching unit or the rear end of the crotch stretching unit, and the crotch stretching unit is positioned between the leg stretch units and independent from the leg stretch units.

* * * * *